US008082031B2

(12) United States Patent
Ochs (10) Patent No.: US 8,082,031 B2
(45) Date of Patent: Dec. 20, 2011

(54) NEUROFEEDBACK SYSTEM

(75) Inventor: Len Ochs, Sebastapol, CA (US)

(73) Assignee: Ochslabs, Inc., Sebastapol, CA (US)

(*) Notice: Subject to any disclaimer, the term of this patent is extended or adjusted under 35 U.S.C. 154(b) by 83 days.

(21) Appl. No.: 12/535,074

(22) Filed: Aug. 4, 2009

(65) Prior Publication Data
US 2010/0036276 A1    Feb. 11, 2010

Related U.S. Application Data

(60) Provisional application No. 61/087,318, filed on Aug. 8, 2008.

(51) Int. Cl.
*A61B 5/04* (2006.01)
(52) U.S. Cl. ...................................................... 600/544
(58) Field of Classification Search .................. 600/544, 600/545
See application file for complete search history.

(56) References Cited

U.S. PATENT DOCUMENTS

| 5,036,858 | A | 8/1991 | Carter et al. | |
|---|---|---|---|---|
| 5,365,939 | A | 11/1994 | Ochs | |
| RE36,348 | E | 10/1999 | Carter | |
| 2004/0002635 | A1* | 1/2004 | Hargrove et al. | 600/300 |
| 2006/0258950 | A1 | 11/2006 | Hargrove et al. | |
| 2009/0281447 | A1 | 11/2009 | Gerdes | |

* cited by examiner

*Primary Examiner* — Patricia Mallari
*Assistant Examiner* — Christian Jang
(74) *Attorney, Agent, or Firm* — Edward S. Sherman (57) ABSTRACT

An apparatus and process for low energy neurofeedback includes computer and display means on a general purpose computer to calculate and display dominant brain wave frequencies as measured by an electroencephalogram. The general purpose computer is also operative to compute and display a new frequency that is offset from the dominant frequency by 5 to 20 Hz. A therapeutically beneficial low power RF field is generated in the EEG leads merely by the computation and display of the new frequency without the need to deliberately power the EEG leads.

11 Claims, 9 Drawing Sheets

NEUROFEEDBACK SYSTEM

CROSS REFERENCE TO RELATED APPLICATIONS

The present application claims priority to the U.S. provisional patent application of the same title filed on Aug. 8, 2008, having application Ser. No. 61/087,318, which is incorporated herein by reference.

BACKGROUND OF INVENTION

The present invention relates to an apparatus and method of brain therapy using neurofeedback, and in particular to an improved method and apparatus for low energy neurofeedback.

Generally speaking, neurofeedback is a method of treating physical or psychological disorders having some form of organic brain dysfunction. Various methodologies involve recording the brain electrical activity from pattern of electrical leads placed on and around the scalp, known as an electroencephalograph or EEG.

The EEG reveals periodic variations in electrical activity within the brain, which has traditionally been characterized as combinations of four frequency bands or components; which are delta, theta, alpha, and beta. While the state of consciousness is the primary cause of one frequency being dominant over the other, subtle variations in these components frequently indicate underlying disorders. During sleep, delta waves having a frequency of four hertz (Hz) are dominant. Theta waves (4 to 8 Hz) are associated with the twilight consciousness on the brink of sleep, during which dreamlike mental images can surface. At higher frequency still are alpha (8 to 12 Hz), which are dominant in the calm and mentally unfocused state typically connected with relaxation. Beta waves, from 12 to 35 Hz are dominant in the normal waking state, when our eyes are open and focused on the world. When the patient is relaxed but alert the beta waves tend to be at the lower frequency range of 12 to 15 Hz, whereas in the excited, anxious state the beta waves can be as high as 35 Hz. Early EEG neurofeedback focused on helping people learn to generate waves associated with deep relaxation: alpha and theta. Other treatment modalities evolved in which the patient received a stimulus based on the results of the EEG.

Although neurofeedback modifies the brain function in a manner not fully understood, such treatments are now well correlated with therapeutic benefits for many types of disorders. Further, changes in a patient's EEG can also reveals that the brain function is modified by the feedback.

One such method is more fully described in U.S. Pat. No. 5,365,939 (issued to Ochs on No. 22, 1994), and U.S. Pat. No. 5,036,858 (issued to Carter et al. on Aug. 6, 1991 and re-issued as RE 36,348 on Oct. 19, 1999), both of which are incorporated herein by reference. The feedback to the patient is via goggles that contain light emitting diodes (LEDs), but may also include sounds. The treatment, via the output of LED's, was accomplished at two different frequencies, but always within a predetermined range of the current actual brain wave frequency and the desired frequency. The apparatus to accomplish this method had a computer processor, a computer memory, EEG electrodes along with an amplifier, a programmable timing generator responsive to the computer processor for generating the two frequencies, audio amplifiers and a beat frequency generator driving a visual frequency amplifier.

It was subsequently discovered that the patient did not need to actually see the LEDs in the goggles for the therapy to have a benefit. The LEDs could be masked or completely blocked and the patient would still show clinical improvement. It was surprisingly discovered that very low electric fields generated by the power to the LEDs in the goggles was therapeutically effective.

Figure 1:
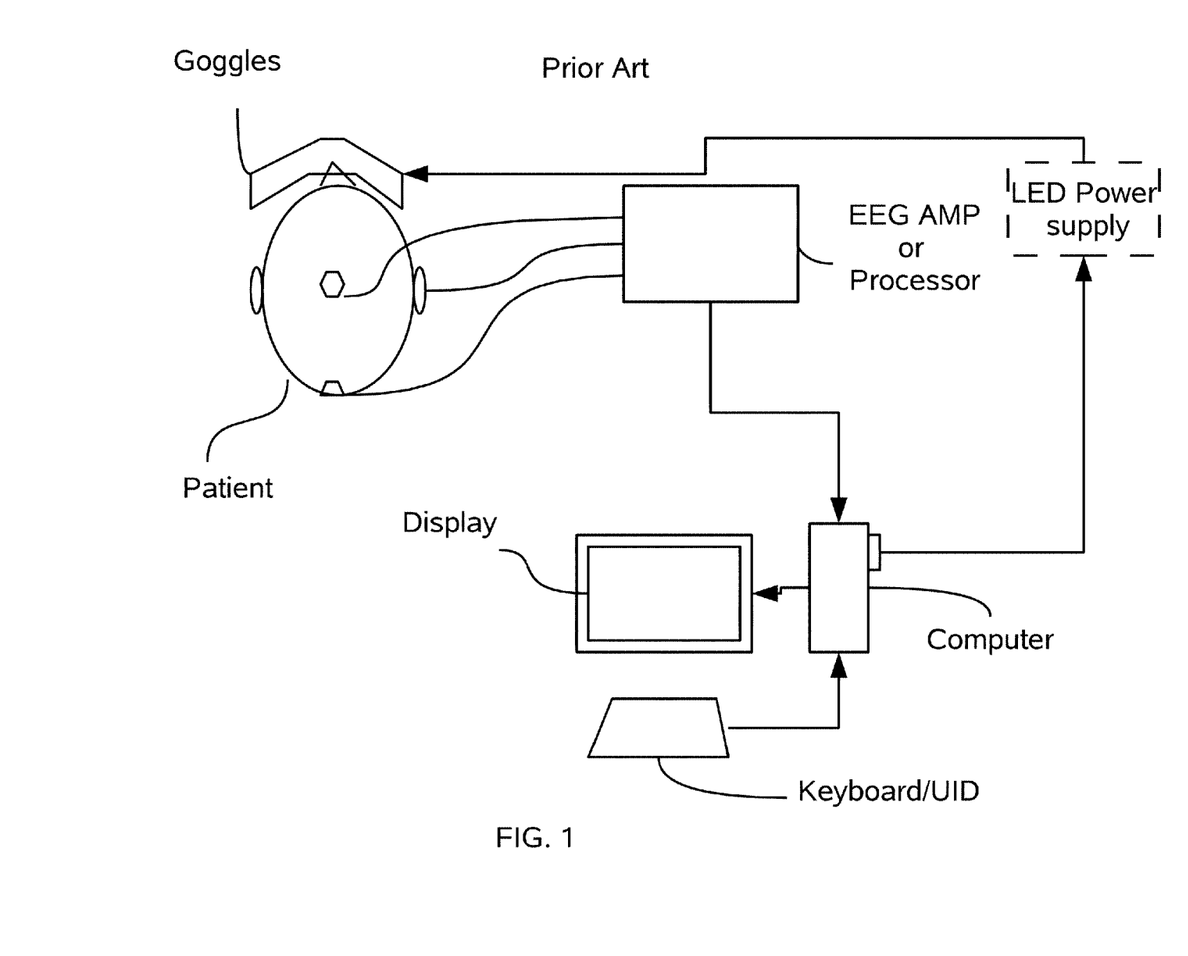
FIG. 1 is a schematic illustration of a prior art apparatus used to treat individuals by neurofeedback based on the analysis of the EEG, known at the time as disentrainment feedback.
Figure 2:
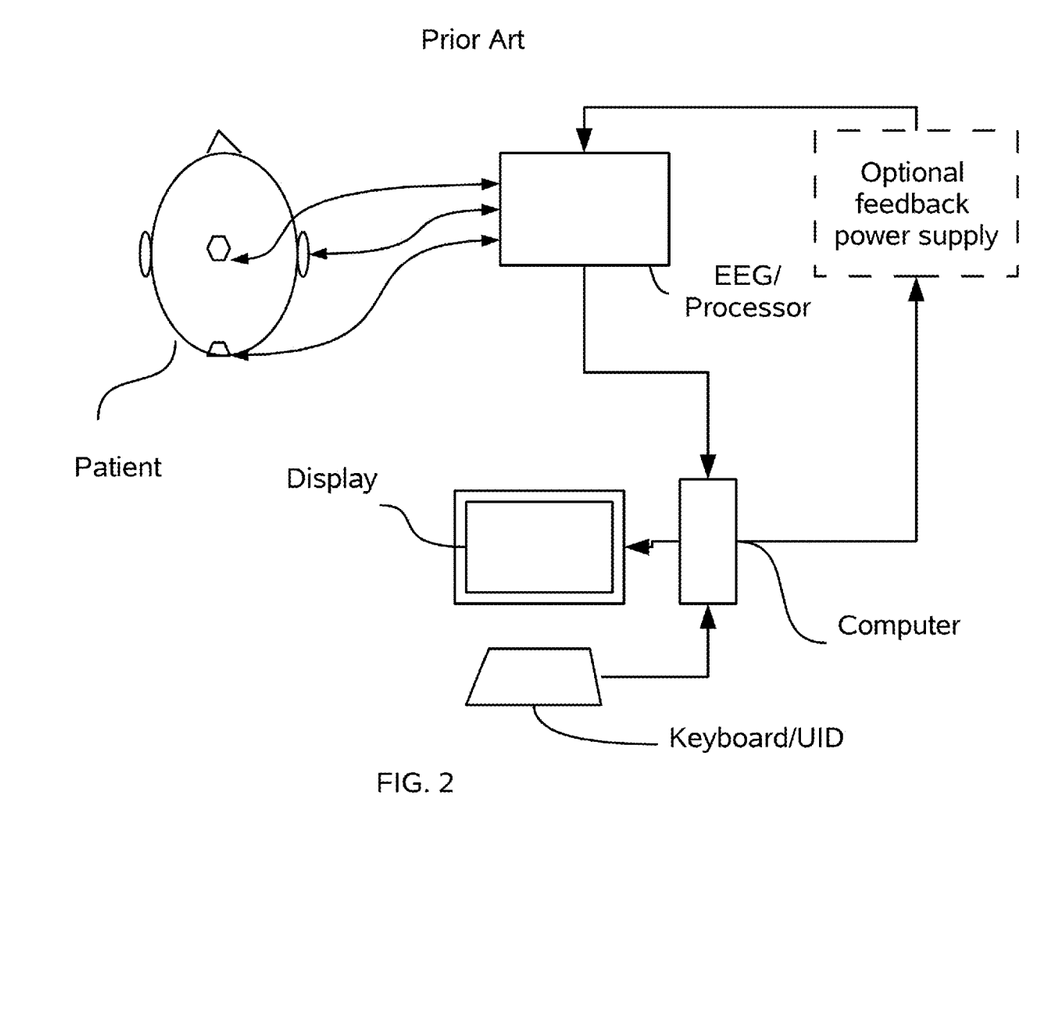
FIG. 2 is a schematic illustration of another prior art apparatus used to treat individuals with EEG by neurofeedback that represented an improvement over that shown in FIG. 1.

This discovery then led to the state of the art Low Energy Neurofeedback System, or LENS, of which an exemplary system for such treatment is shown in FIG. 2. The LENS method employs extremely weak intensities of feedback and does involve the patient's own EEG driving the feedback, but does not involve any conscious participation or even positive intention. The LENS works by continuously monitoring EEG activity and then uses these readings to determine the frequency of very small electromagnetic fields that are "offset" several cycles per second (hertz) faster than the patient's dominant brainwave. LENS uses an electromagnetic field as the carrier wave for the feedback. With this method, the EEG leads serve as bi-directional conduits for both the brainwaves and the feedback signals. This feedback stimulus input is then delivered down electrode wires at generally seven or fewer electrode sites in the course of a treatment session, for only one second per site. This input is much weaker than what the brain receives from holding a cell phone to one's ear, the power being in the range of nano-watts/cm2. The LENS approach is reviewed in the Journal of Neurotherapy, Vol 10, no. 2/3, 2006, pp. 5-39, which is incorporated herein by reference.

In the LENS method either the computer or a microprocessor associated with EEG amplifier performs the calculations based on the EEG and then delivers power to different leads placed on the patient's scalp. The exact order of treatment, power, duration and like parameters depends on the clinical findings, and in particular an initial evaluation of the patient's sensitivity to treatment.

Figure 3:
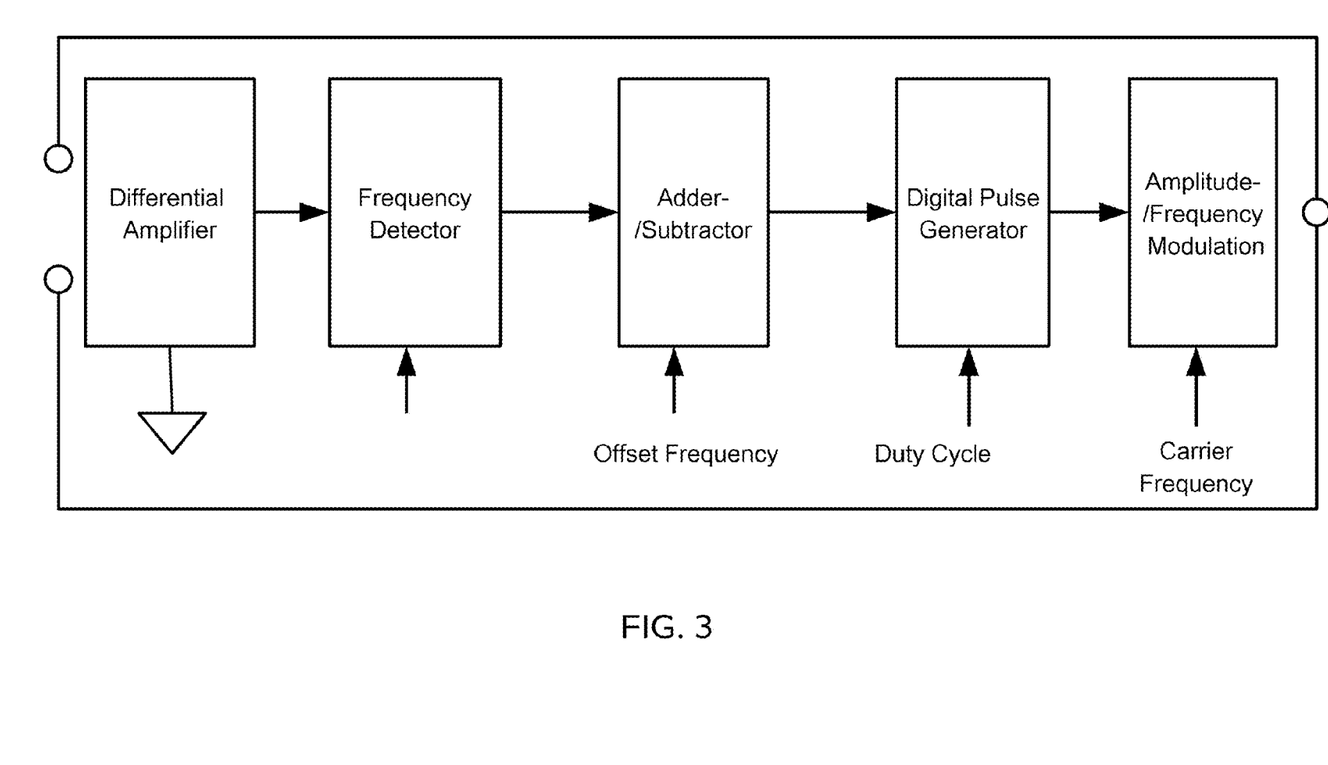
FIG. 3 is a schematic illustration of the EEG amplifier with an embedded microprocessor used in the apparatus of FIG. 2, used to treat individuals in the LENS method of neurofeedback.

A block diagram of the LENS system is shown in FIG. 2, while the components of microprocessor associated with generating the feedback signal are illustrated in FIG. 3. The EEG Amplifier/microprocessor of FIGS. 2 and 3 that is used to acquire the EEG and provide the feedback stimulus may be acquired from J&J Engineering Incorporated, 22797 Holgar Ct. Nebr., Poulsbo, Wash. 98370, subject to restrictions customary for medical devices. As the microprocessor of FIGS. 2 and 3 is not needed to deploy the current invention it will not be described further. However, it should be appreciated that due to its components and complexity it adds significantly to the expense of the neurofeedback equipment. The software that interfaces with the EEG acquisition system of J & J Engineering for the LENS method is available from OchsLabs, 8151 Elphick Lane, Sebastopol, Calif. 95472, subject to similar restrictions. The software aids in the clinician's diagnosis, treatment plan development and actual treatment based on the LENS protocols, which vary depending on the patient's condition and the reason for treatment, among other factors.

It is a primary object of the present invention to provide a means for LENS treatment that does not require the special microprocessor and associated hardware required to power the EEG leads.

SUMMARY OF INVENTION

In the present invention, the first object is achieved by providing an apparatus for low energy neurofeedback treatment, the apparatus comprising a plurality of EEG leads for attachment to the patient, an EEG amplifier in signal communication with said EEG leads, the EEG amplifier consisting essentially of means to amplify signal received from the leads attached to the patient. A computer is also in signal communication with said EEG amplifier to acquire and display the EEG. At least one of computer and EEG amplifier further comprises computational means to determine the dominant frequency in each EEG lead pair. The computer also comprises a user interface for providing a predetermined offset frequency, computation means to calculate a prospective treatment frequency by summing the predetermined offset frequency and the dominant frequency, wherein the calculated prospective treatment frequency is not feedback in an amplified form to the EEG leads.

A second aspect of the invention is characterized by a method for low energy neurofeedback treatment, the method consisting essentially of the steps of providing a EEG amplifier in signal communication with a patient, providing a general purpose computer in signal communication with the EEG amplifier to receiver, analyze and display the patient EEG and to calculate a prospective treatment regimen, acquiring one or more EEG signals from the patient in the EEG amplifier, converting the analog EEG signals to a digital format, determining the dominant frequency of the EEG signals in the general purpose computer, calculating a prospect treatment regimen in the general purpose computer, said step of calculating further comprising the step of providing a frequency offset value, calculating a prospective treatment frequency by summing the dominant frequency and frequency offset value, displaying dominant frequency, frequency offset and prospective treatment frequency on the monitor associated with the general purpose computer.

The above and other objects, effects, features, and advantages of the present invention will become more apparent from the following description of the embodiments thereof taken in conjunction with the accompanying drawings.

BRIEF DESCRIPTION OF THE DRAWINGS

FIG. 7A illustrates an EEG in time domain, whereas

DETAILED DESCRIPTION

Referring to FIGS. 1 through 9, wherein like reference numerals refer to like components in the various views, there is illustrated therein a new and improved neurofeedback system, generally denominated 100 herein.

Figure 4:
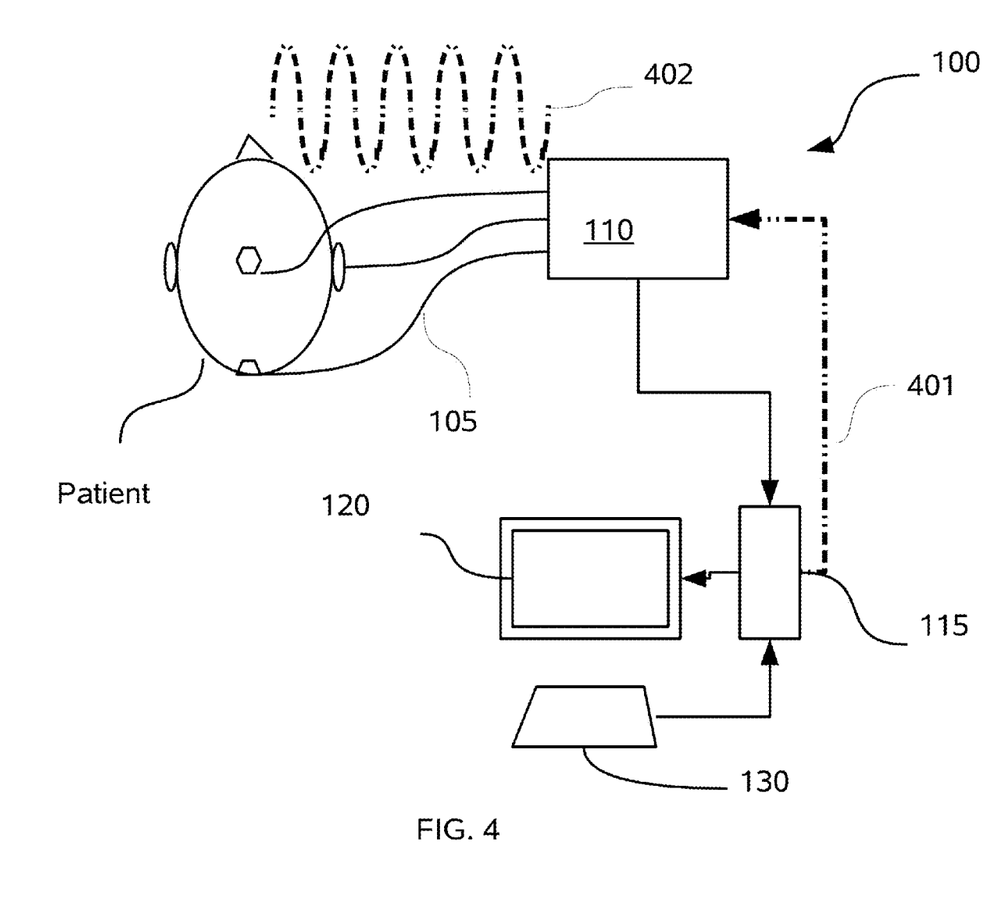
FIG. 4 is a schematic illustration of the inventive apparatus for LENS treatment.

In accordance with the present invention, FIG. 4 is a schematic illustration of the inventive apparatus for LENS treatment. The system comprises a plurality of EEG leads 105 connected to the patient, an EEG amplifier 110 in signal communication with the EEG leads 105 and a general purpose computer 115 in signal communication with the EEG amplifier 110.

The EEG amplifier 110 may provide the general purpose computer 115 with amplified analog signals provided the computer also has an A/D converter, or the A/D converter may reside in the EEG amplifier. It should be appreciated that the EEG amplifier 110 serves to collect the relatively weak EEG signals via the leads and amplify them sufficiently for analysis by the general purpose computer. Such commercial EEG amplifier include A/D converters and generally also have the means to perform an Fast Fourier Transform (FFT) to converter the time domain EEG to a frequency domain resulting in a power spectrum. Furthermore, such commercial instruments also generally will provide at least one of the instantaneous or time average integral of amplitude or power over each of the characteristic wavelengths; delta, theta, alpha, and beta. Thus, such commercial EEG's amplifier are also generally sold with software for use with a general purpose computer for the display, analysis and manipulation of the EEG spectral data. Therefore, such a general purpose computer 115 also comprises a display 120, which preferably deploys a graphic user interface and a key board 130 or equivalent user interface so that the user can control the computer 115 and the course of treatment, as is determined from the patient EEG spectral analysis. The EEG amplifier 110 need not serve the purpose of the EEG amplifier/microprocessor of the prior art device of FIG. 1-3.

What is currently believed to be an unamplified feedback from the computer to the EEG amplifier is shown as line 401 in FIG. 4, which is believed to continued as unamplified feedback from the EEG amplifier to the patient as shown by 402.

It should be understood that the functions of the EEG amplifier and the general purpose computer can also be integrated into one device, as for example configuring the EEG amplifier as a card that plugs into the backplane of the general purpose computer or another port, as well as providing an appropriate computer microprocessor in the same box as the EEG amplifier.

Figure 5:
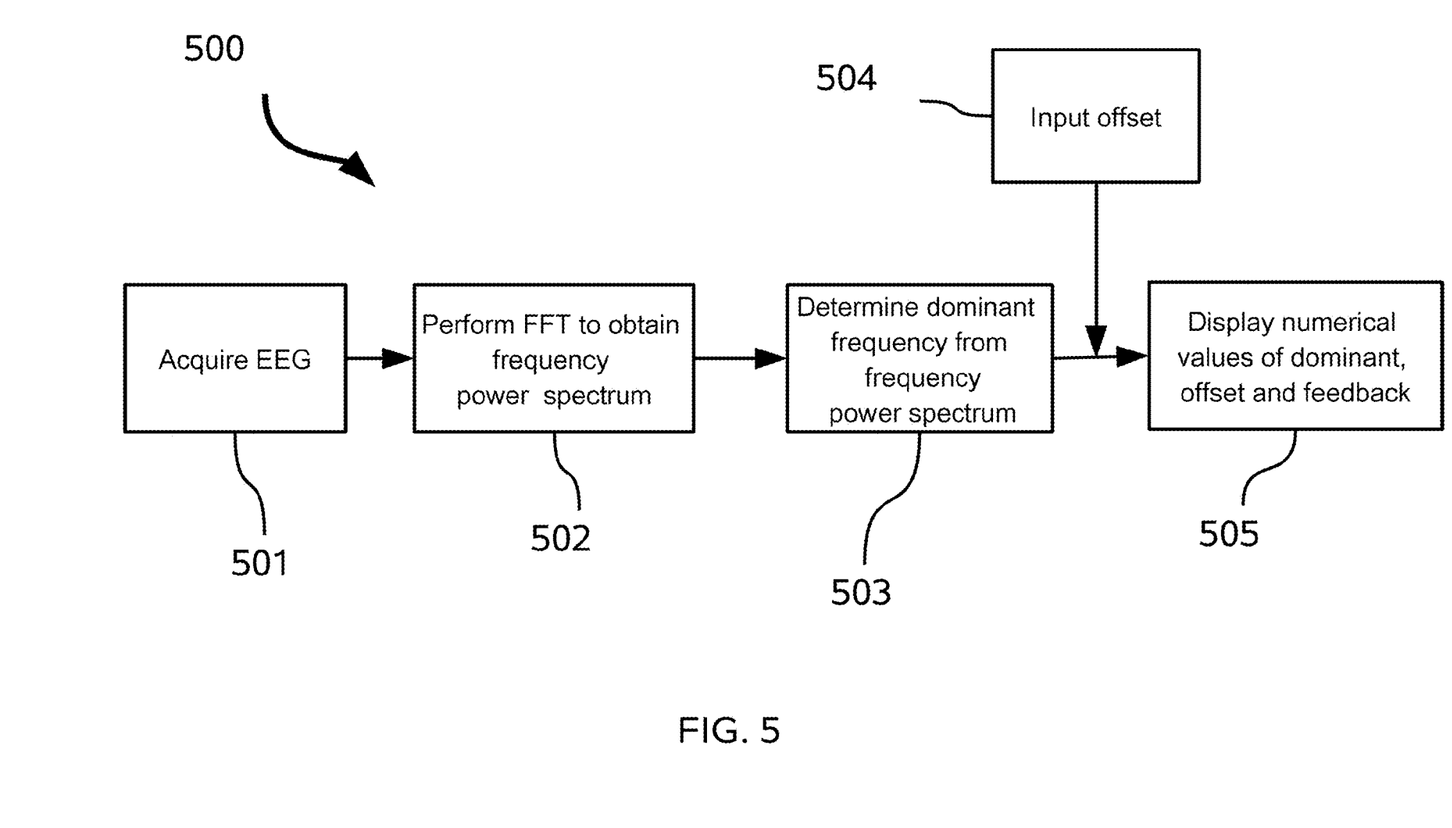
FIG. 5 is a flow chart for the inventive treatment process that deploys the apparatus of FIG. 4.

FIG. 5 is a flow chart of the treatment method using the apparatus 100 of FIG. 4. In the first step 501 of the treatment process 500, the EEG is acquired as a time domain electrical signal. The signal is then digitized and the power spectrum is calculated by a FFT in step 502 to provide the EEG in frequency domain. In the next step, 503 the dominant frequency is identified. In step 504 the user is able to select either directly, or through a pre-programmed option a treatment plan that deploys one or more predetermined offset frequency values, typically between about 5 and 20 Hz. In the final step, 505, the prospective treatment frequency, as referred to herein as "feedback" is calculated as the sum of the predetermined offset frequency and the offset frequency. It is preferable that intermediate results of this process are displayed to the clinician using the equipment.

Figure 6:
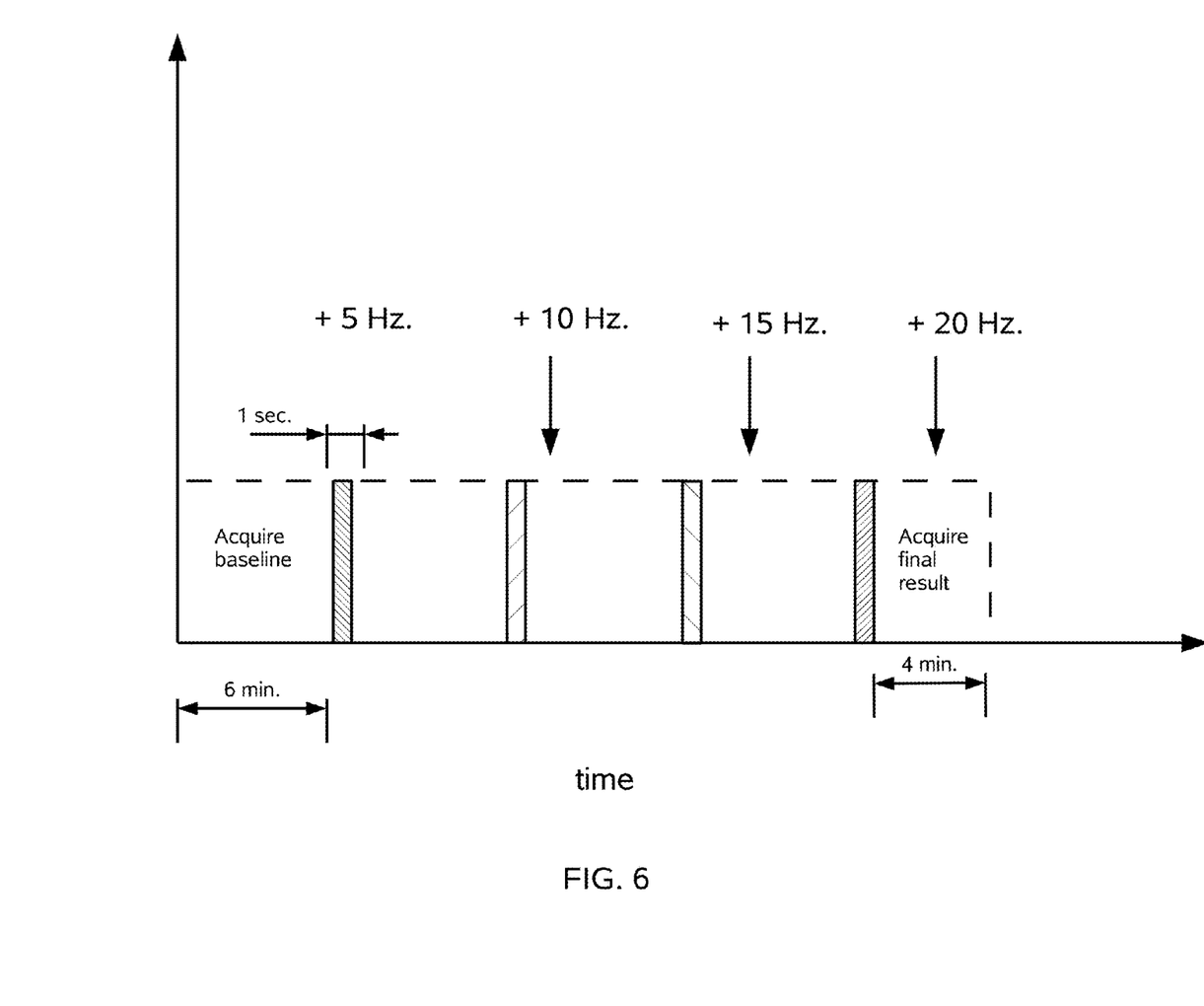
FIG. 6 is a timing diagram of the patient evaluation protocol used in the LENS method.

FIG. 6 is a timing diagram of a preferred patient evaluation protocol. The EEG is acquired (step 501) for about 6 minutes. Then the prospective treatment is provided for a total during of 1 sec., during which the calculation and display are updated every 1/16 sec. Generally it is desirable to report to the clinician the instantaneous power or integrated power in each of the frequency bands delta, theta, alpha, and beta. Following analysis of the EEG as described above the patient is treated for one second under a first treatment condition as a result of the calculation step 505. The treatment is merely the calculation and display of the dominant frequency, the predetermined offset and the prospective treatment or feedback frequency repeated each 1/16 sec. for a total of 1 second. In clinical practice the treatment time may be extended or reduced depending on the patient sensitivity.

The dominant frequency is recalculated each 1/16 of a second from the last 16 measurements. Thus to the extent that this treatment is changing the EEG, the prospective treatment will change during this one second treatment period. It should be understood that the result of the calculation is deemed a prospective treatment frequency because there is no further active generation and delivery of a treatment to the patient by additional hardware or software components.

Following this one second treatment the EEG is then acquired for 60 seconds and a new baseline is determined. Prior to the next treatment in the patient evaluation process, at the end of 60 seconds, the dominant frequency is again recalculated each 1/16 of a second from the last 16 measurements. A second treatment of a 1 sec. duration is then provided by recalculating the sum of each new dominant frequency and the proscribed offset value. The process of 60 seconds of baseline EEG acquisition followed by 1 second of treatment is repeated for a total of four times. In the first treatment the calculated or prospective treatment is the calculated using the offset value of 5 Hz. In each of the three subsequent treatments the offset value added to the dominant frequency increases by an increment of another 5 Hz. from the previous treatment. The last stage of the protocol is to acquire a final EEG for 4 minutes. This evaluation protocol is illustrated as a timing diagram in FIG. 6.

No wishing to be bound by theory, it is currently believed that the process of calculation generates a very weak feedback of energy back to the EEG processor and on to the patient via the leads without further deliberate amplification. As will be shown in comparative examples below in FIG. 8A-C, the result of the calculation is apparent with various brands of EEG amplifiers.

Figure 7A:
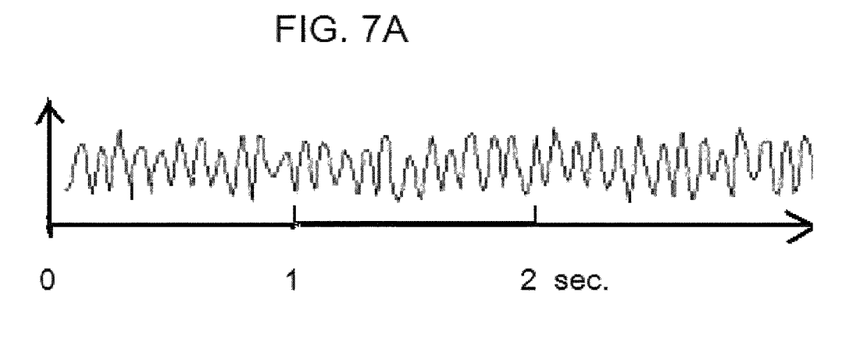
Figure 7B:
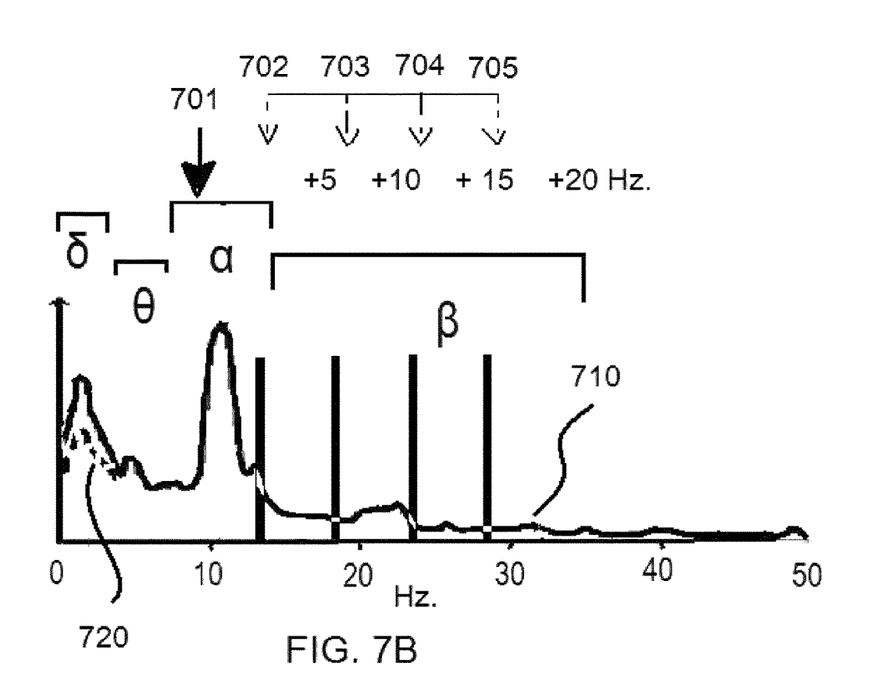
FIG. 7B is an exemplary power spectrum derived by an FFT of a time domain EEG such as that in FIG. 7A.

Thus, a typical EEG spectrum, as received and optionally display at the general purpose computer in time domain is shown in FIG. 7A. FIG. 7B illustrates how data acquired from the EEG are then analyzed so that the appropriate feedback can be applied to the patient. In FIG. 7B a typical power spectrum obtained from the FFT shown peaks in the frequency bands known as alpha, beta, theta and delta, indicated by the corresponding Greek letter above the spectrum. As the FFT provides a relative intensity of the different components at all frequencies, the displayed and calculated frequency of the Delta waves, about 0-4 Hz. is merely the sum of either the power or amplitude of all frequency components in the band, indicted by the letter δ.

The dominant frequency is the arithmetic mean of frequency across all values across the entire power spectrum from 0 to 35 Hz, which is δ to β, and is generally indicated by arrow 701. Arrows 702, 703, 704 and 705 then represent the treatment protocols that would normally be applied in the patient evaluation stage where the microprocessor and associated hardware send a constant frequency signal back onto the EEG leads in the prior art method, or the result of the general purpose computer calculating a feedback value as a prospective treatment as disclosed herein.

The first power spectrum 710 represents an average of what might be acquired during the initial 6 minutes before the start of treatment. Because of temporal variation of the EEG in all patients, the average of all such power spectrums over 6 minutes is considered a baseline result for the purpose of evaluating the treatment method to determine the proper offset value for further treatment. In contrast, the second power spectrum, 720, a superimposed broken line, presents a typical result representative of the average of all EEG's that might be acquired over the last 2 minutes, after actual treatment in the prior art method, or the prospective treatment described herein. While the changes in the second power spectrum vary from patient to patient in subtle ways, these power spectrums 701 and 702 are theoretical to illustrate the general trend of a drop in the amplitude with the delta wave band of the spectrum, which also correlates well with therapeutic benefit to the patient.

Comparative Examples

Figure 8A:
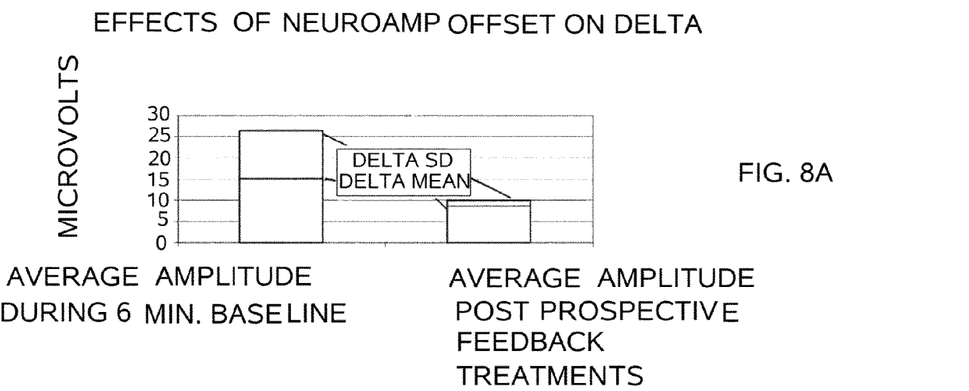
FIG. 8A-C is a graphic illustration of the results of the comparative treatment examples using the apparatus of FIG. 4.
Figure 8B:
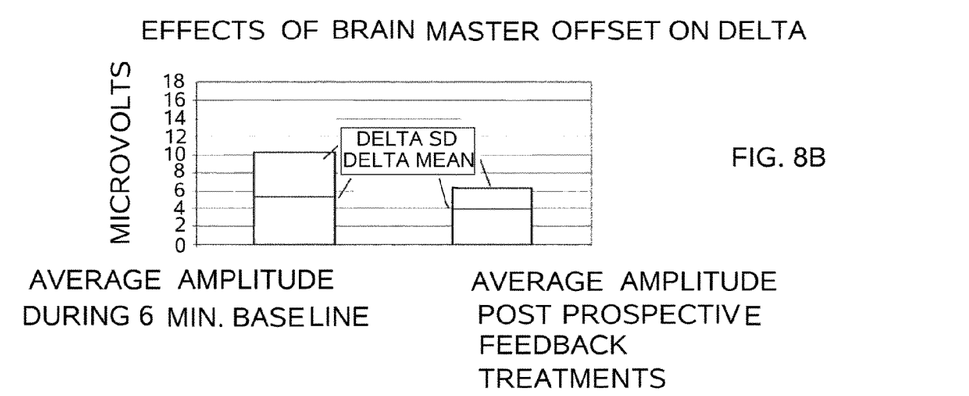
Figure 8C:
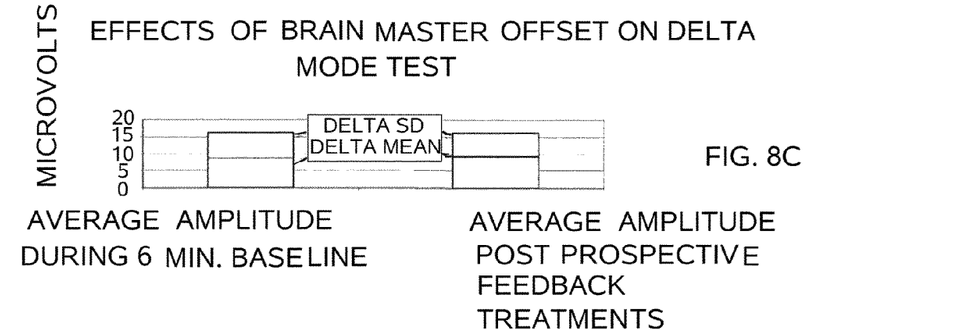

The average of the changes, between the baseline characterization for 6 minutes, and the last 2 minutes at the end of 4 treatment cycles of the timing diagram of FIG. 5 are summarized in the bar graphs of FIG. 8A-C for two different brands of EEG amplifiers, neither of which was used in a mode capable of amplifying the result of the calculation and feeding it back to the patient at higher power on the EEG leads.

For both commercial EEG amplifiers evaluated in these comparative examples, the software provided by the amplifier manufacturer was modified to enable the process shown in FIG. 5. This software, which runs on the general purpose computer that is supplied with each of the commercial EEG amplifiers was coded as shown in the flow chart in FIG. 9. In all cases the results of the calculation where displayed on the computer monitor.

The therapeutic effect, a decrease in Delta wave band amplitude, is further substantiated by the results shown in FIGS. 8A, B and C. In these bar graphs first bar on the left illustrates the average Delta amplitude over the 6 min. baseline. The lower horizontal line across each bar shows the average power of the dominant frequency in the delta wave frequency range, in microVolts averaged over test of a group of patient. The upper horizontal line shows the standard deviation for the initial baseline of 6 minutes. The second bar on the right (feedback) shows the resulting average amplitude in the delta wave band the final 4 minutes of the evaluation protocol of FIG. 5. Thus, each patients had been exposed to whatever prospective treatment is generative by the method 500 of FIG. 5 for a total of 4 seconds.

Figure 9:
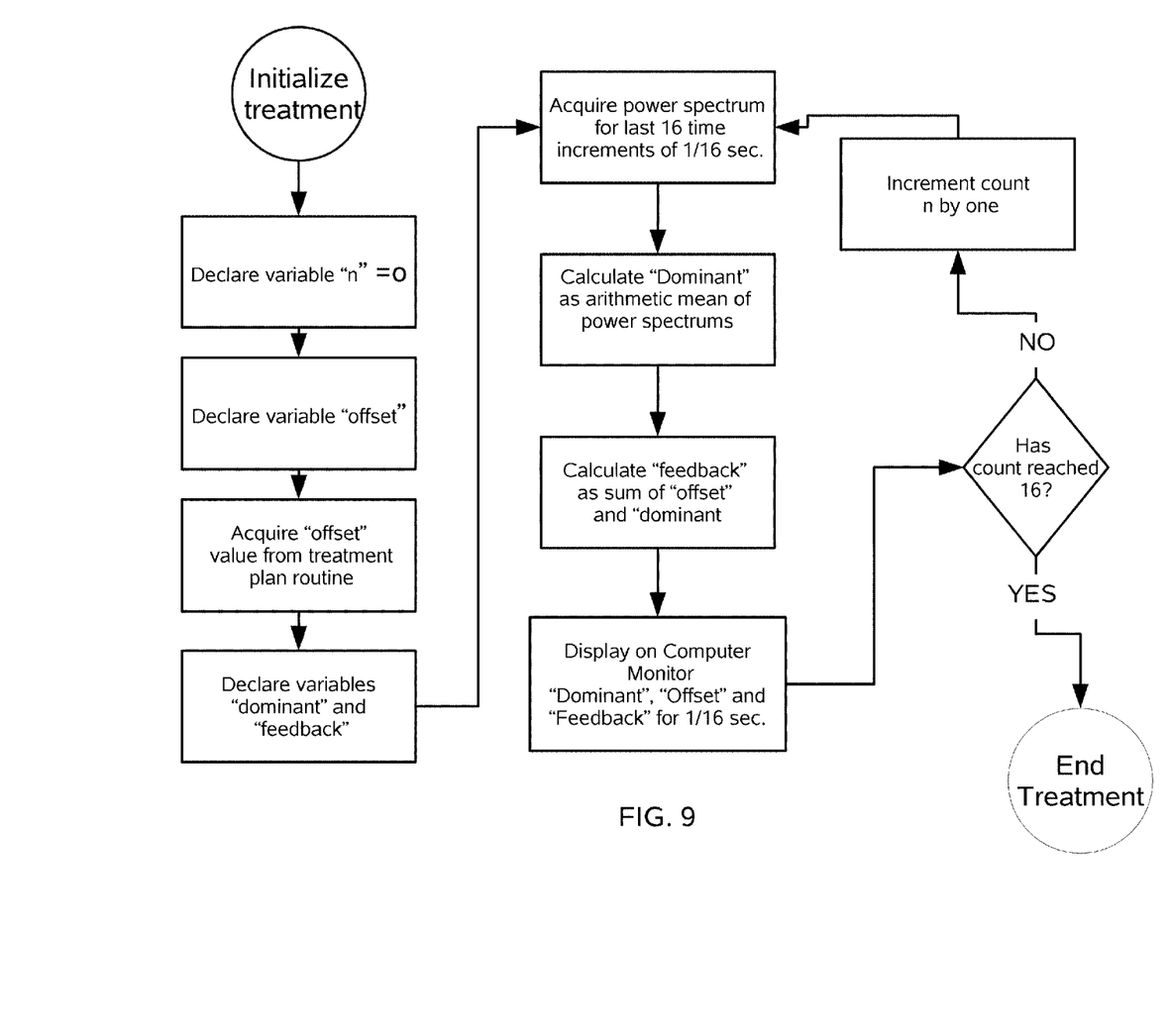
FIG. 9 is a flow chart of the general code deployed in the comparative examples in FIGS. 8A and B.

Specifically, FIG. 8A shows the results when an Othmer NeuroAmp brand EEG amplifier was used with a general purpose computer as programmed in FIG. 9. This result is the average from two subjects using the protocol of FIG. 6. The decrease in average delta wave amplitude is comparable to what is observed when the amplified feedback is provided through a microcoded J&J I-330 C2 EEG in the method described with respect to FIG. 2 and FIG. 3. The NeuroAmp brand EEG amplifier is available from EEG Info, 22020 Clarendon St. Suite 305, Woodland Hills, Calif. 91367.

FIG. 8B show comparable results when a BrainMaster Atlantis 2×2 Model EEG amplifier was used to acquire the EEG. This model is available from BrainMaster Technologies, Inc. 24490 Broadway Avenue, Oakwood Village, Ohio 44146. Again the formula of step 505 in FIG. was programmed within the computer according to FIG. 9, rather than microprogrammed on a on-board microprocessor inside the EEG amplifier. This graph represents the averages from ten subjects. Again this produced a result of therapeutic significance as the average amplitude of the Delta frequency band has decreased.

FIG. 8C is a comparative result with the BrainMaster EEG amplifier again used with 10 subjects. However the prospective treatment frequency, or "feedback" variable, was calculated as the sum of the modal frequency plus the offset, and not the dominant frequency. The modal frequency is the frequency in the power spectrum with the highest amplitude. No drop in Delta wave amplitude was observed. This is consistent with prior experience in the early years of experimentation with the prior art microprogrammed system, during which it was discovered that deploying a feedback based on the modal frequency was much less effective in reducing the Delta wave band amplitude.

It should now be noted as shown in FIGS. 8A and 8B that two different brands of EEG amplifiers are compatible with the discovery that the calculation of a prospective treatment frequency in the general purpose computer is sufficient to obtain the result of the decrease in intensity of the delta wave amplitude. This larger decrease in integrated Delta wave amplitude correlates well with therapeutic benefits reported by patients. Not wishing to be bound by theory, It is currently believed that the greater decrease in Delta wave activity observed with NeuroAmp device, as compared with the BrainMaster device is from the larger electromagnetic field generated by the device. That is, the signal that reaches the computer 115 is already at a higher power, hence any feedback from the calculation is also at a higher power.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

The invention claimed is:

1. A method for low energy neurofeedback treatment, the method consisting essentially of the steps of:
   a) providing an EEG amplifier in signal communication with a patient,
   b) providing a general purpose computer in signal communication with the EEG amplifier to receive, analyze, and display EEG signals from the patient and to calculate a prospective treatment regimen,
   c) acquiring one or more analog EEG signals from the patient in the EEG amplifier,
   d) converting the one or more analog EEG signals to a digital format,
   e) determining the dominant frequency of the one or more analog EEG signals in the general purpose computer,
   f) calculating the prospective treatment regimen in the general purpose computer, said step of calculating further comprising:
      i) providing a frequency offset value,
      ii) calculating a first prospective treatment frequency by summing the dominant frequency and the frequency offset value,
   g) redetermining the dominant frequency each $1/16$ of a second from the last 16 measurements and further recalculating the prospective treatment regimen for each redetermined dominant frequency.

2. The method for low energy neurofeedback treatment according to claim 1 further comprising a step of displaying the dominant frequency, the frequency offset, and the prospective treatment frequency on a monitor associated with the general purpose computer.

3. The method for low energy neurofeedback treatment according to claim 2 wherein the step of displaying the dominant frequency, the frequency offset, and the prospective treatment frequency on the monitor associated with the general purpose computer is repeated every $1/16$ of a second for a time interval of at least one second.

4. The method of claim 3 wherein the calculated prospective treatment frequency is not feedback in an amplified form to the EEG leads.

5. The method of claim 2 wherein the calculated prospective treatment frequency is not feedback in an amplified form to the EEG leads.

6. The method of claim 1 wherein the calculated prospective treatment frequency is not feedback in an amplified form to a plurality of EEG leads.

7. The method of claim 1 wherein the calculated prospective treatment frequency is not feedback in an amplified form to a plurality of EEG leads or as a photic stimulation.

8. An apparatus for low energy neurofeedback treatment, the apparatus consisting essentially of:
   a) a plurality of EEG leads, wherein the leads are adapted to be attached to the patient,
   b) an EEG amplifier in signal communication with said EEG leads, the EEG amplifier consisting essentially of means to amplify signal received from the leads attached to the patient,
   c) a computer in signal communication with said EEG amplifier to acquire and display an EEG signal,
   d) at least one of the EEG amplifier and computer comprising computational means to determine the dominant frequency in each EEG lead pair,
   e) the computer further comprising:
      i) a user interface for providing a predetermined offset frequency,
      ii) computation means to calculate a prospective treatment frequency by summing the predetermined offset frequency and the dominant frequency, wherein the calculated prospective treatment frequency is not feedback in an amplified form to the EEG leads or used to provide photic stimulation.

9. An apparatus for low energy neurofeedback treatment, the apparatus comprising:
   a) a plurality of EEG leads, wherein the leads are adapted to be attached to the patient,
   b) an EEG amplifier in signal communication with said EEG leads, the EEG amplifier consisting essentially of means to amplify signal received from the leads attached to the patient,
   c) a computer in signal communication with said EEG amplifier to acquire and display the an EEG signal,
   d) at least one of the EEG amplifier and computer comprising computational means to determine a dominant frequency in each EEG lead pair,
   e) the computer further comprising:
      i) a user interface for providing a predetermined offset frequency,
      ii) computation means to calculate a prospective treatment frequency by summing the predetermined offset frequency and the dominant frequency, and compute a new dominant frequency each $1/16$ of a second from the last 16 measurements, wherein the calculated prospective treatment frequency is not feedback in an amplified form to the EEG leads.

10. An apparatus for low energy neurofeedback treatment according to claim 9, the apparatus further comprising a means for displaying the dominant frequency, the frequency offset, and the prospective treatment frequency.

11. An apparatus for low energy neurofeedback treatment according to claim 10, wherein the means for displaying the dominant frequency, the frequency offset, and the prospective treatment frequency is a monitor associated with the computer.

* * * * *